United States Patent [19]

Lennon et al.

[11] Patent Number: 5,083,557
[45] Date of Patent: Jan. 28, 1992

[54] DISPOSABLE PODIATRY BOOT

[75] Inventors: Patrick G. Lennon, Green Bay; Andrea L. Potokar, DePere, both of Wis.

[73] Assignee: Little Rapids Corporation, Greenbay, Wis.

[21] Appl. No.: 562,167

[22] Filed: Aug. 3, 1990

[51] Int. Cl.⁵ ............................................ A61F 13/00
[52] U.S. Cl. .................................... 128/82; 128/849; 128/882; 128/157
[58] Field of Search ................. 128/849, 82, 882, 157, 128/846, 91 R, 856

[56] References Cited

U.S. PATENT DOCUMENTS

| | | | |
|---|---|---|---|
| 1,980,486 | 11/1934 | King | 128/882 |
| 4,178,924 | 12/1979 | Baxter | 128/82 |
| 4,523,586 | 6/1985 | Couri | 128/82 |
| 4,722,143 | 2/1988 | Everett | 128/82 |
| 4,727,864 | 3/1988 | Weisenthal | 128/82 |

Primary Examiner—Robert A. Hafer
Assistant Examiner—David J. Kenealy
Attorney, Agent, or Firm—Niro, Scavone, Haller & Niro

[57] ABSTRACT

A disposable podiatry boot especially useful for protecting casts or dressings from moisture comprises a sock-shaped member of thin water-impervious material. The sock-shaped member is provided with traction means and an integral fastening means for securing it in place on the leg of the user and providing a watertight seal.

2 Claims, 1 Drawing Sheet

DISPOSABLE PODIATRY BOOT

FIELD OF THE INVENTION

This invention relates to a podiatry boot of the type that is used by a podiatrist to protect a patient's foot that is in a cast or has a dressing. More particularly, it relates to a disposable podiatry boot with traction means and an integral fastening means for securing the podiatry boot in place on the patient.

BACKGROUND OF THE INVENTION

At the present time, patients with casts and dressings on their feet find it difficult to protect the casts and dressings when taking showers, bathing or during bad weather. The most common form of protection used by those with casts and dressings are plastic garbage bags that are wrapped around the cast or dressing and taped in place with adhesive tape. The use of such plastic garbage bags is not without disadvantages. First, because they are normally much too large for the foot to be protected there is excess material which is unsightly and can interfere with walking. Second, the garbage bags do not provide very good traction so that the user has an increased risk of falling and complicating his injuries and third, it is difficult to fasten the bag securely to form a water tight seal between the garbage bag and the patient's leg.

In the Samuels et al. U.S. Pat. No. 3,416,518 a cast cover is disclosed which is formed of a stretchable elastic material. The Samuels et al. protector is intended to be worn more than once and is too expensive to be disposable.

In the Caplan U.S. Pat. No. 2,229,575, a protector for artificial limbs is disclosed which can be attached to the limb with a draw string and an elastic band to form a watertight seal. The protector has a relatively heavy sole and is not intended to be disposable.

It is an object of this invention to disclose a new and improved disposable podiatry boot which provides superior traction and which can be quickly and securely fastened in place to form a watertight seal.

BRIEF DESCRIPTION OF THE INVENTION

The present invention relates to a disposable podiatry boot for use in protecting a foot with a cast or dressing. The podiatry boot comprises a normally lay-flat sock-shaped member of moisture impervious material which is large enough to receive a foot with a cast or dressing and which has a sole with traction means and an integral fastening means.

The aforementioned objects of the invention will be more readily apparent to those skilled in the art from the drawings and description which follows.

DETAILED DESCRIPTION OF THE INVENTION

In the preferred embodiment of the invention shown in FIGS. 1 to 5 of the drawings, the podiatry boot comprises a sock-shaped member 10 formed of two thin pliable sheets 11, 12 of a water impervious material which are sealed together along their outer edges to form a seal 13. In an especially preferred embodiment, the plastic material of the boot is polyethylene and the seal 13 is formed by heat sealing.

Figure 1:
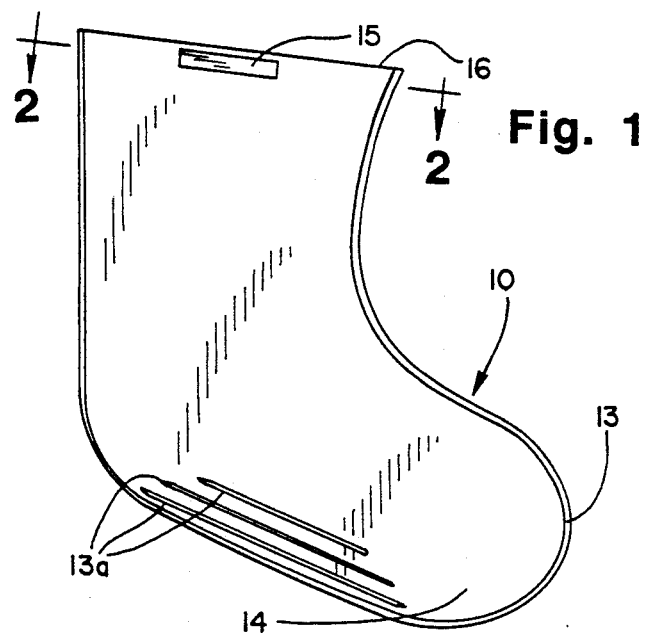
FIG. 1 is a top plan view in elevation of a preferred embodiment of the podiatry boot of the present invention.
Figure 4:
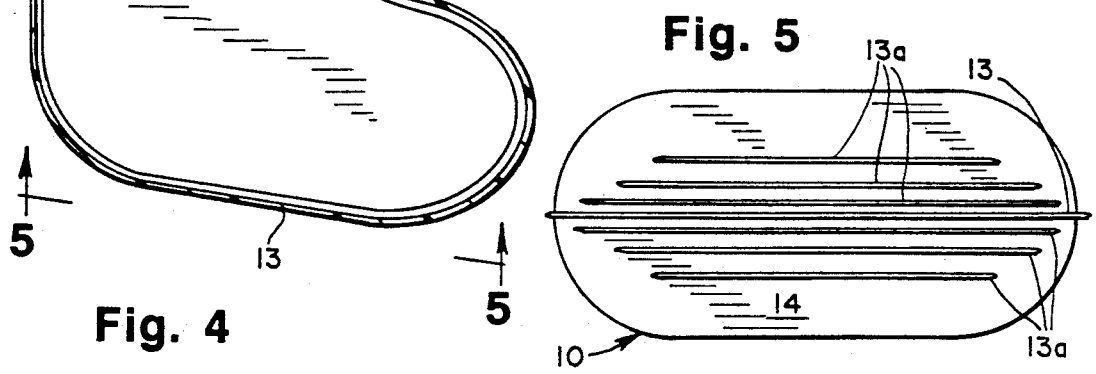
FIG. 4 is a schematic view showing the podiatry boot of FIG. 1 on a patient's leg.
Figure 5:
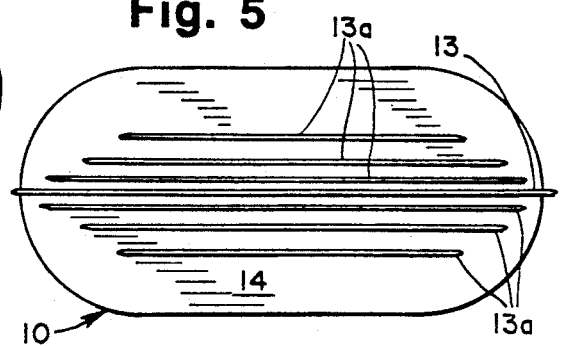
FIG. 5 is a view taken along lines 5—5 in FIG. 1.

As seen in FIGS. 1 and 5, there are additional seals 13a on the sole portion 14 of the member 10. The seals 13a may be formed by sealing portions of the sheets 11, 12 to themself. The seals 13a may be included to provide added traction when the boot is in place as seen in FIG. 4.

Returning to FIG. 1, it also can be seen that the member 10 includes an integral fastening means 15 which is attached to the outside of sheet 11 adjacent to the open top 16.

Figure 2:
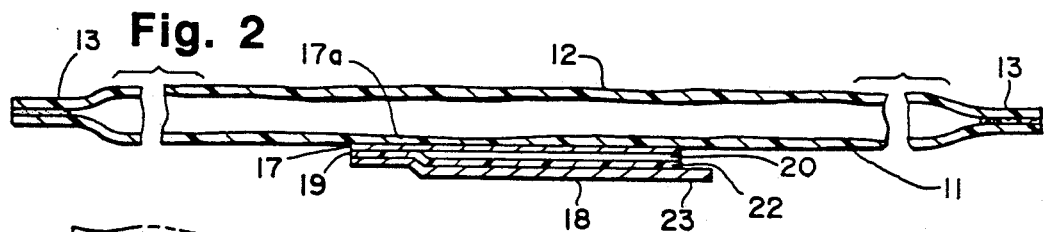
FIG. 2 is a view taken along lines 2—2 in FIG. 1.
Figure 3:
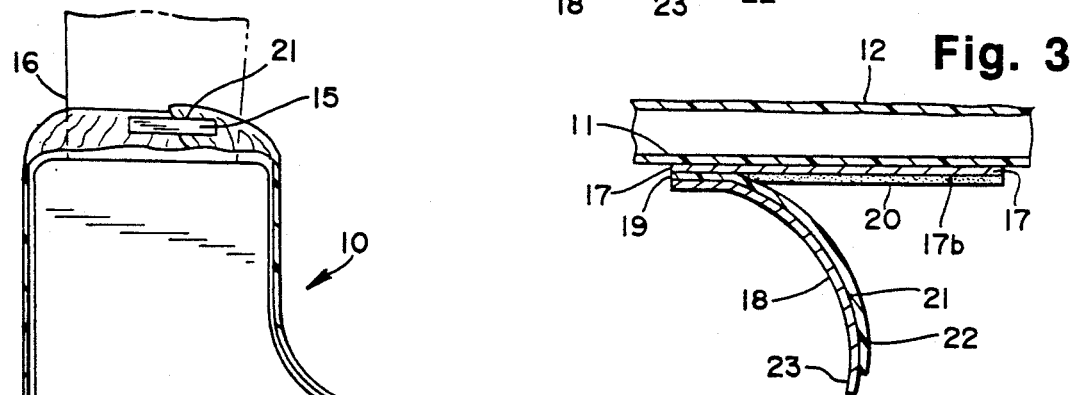
FIG. 3 is an enlarged view of the fastening means seen in FIG. 1 and FIG. 2.

In FIGS. 2 and 3, the fastening means 15 is shown in greater detail. As seen therein, the fastening means 15 comprises an anchoring web 17 and fastening web 18. The anchoring web 17 has one face 17a which is bonded permanently to the outside of the flexible sheet 11. The other face 17b of the anchoring web 17 is bonded at one end with an adhesive 19 to one end of the fastening web 18. The remainder of the other face 17b of the anchoring web 17 is covered with a release coating 20. An intermediate portion 21 of the inner face 18a of the fastening web 18 is coated with a pressure sensitive adhesive 22 and it is, as seen in FIG. 2, releasably stored on the release coating 20. The free end of fastening web 18 which extends past the end of the anchoring web 17 and which is not coated with the pressure sensitive adhesive 22 provides a tab 23.

Referring now to FIG. 3, it can be seen that the intermediate portion 21 of fastening web 18 can be removed from its storage position on the release coating 20 for use in fastening the boot as seen in FIG. 3 by simply lifting it off the release coating 20 with the tab 23.

To form a water-tight seal between the boot and the user's leg, the open top 16 of the boot is first wrapped tightly about the leg, as seen in FIG. 4, and then the intermediate portion 21 with its pressure sensitive adhesive 22 is used to secure the excess material of the open top 16 in place. When the boot is in place, as seen in FIGS. 4 and 5, the seals 13 and 13a are under the user's foot where they provide traction.

It will be appreciated by those skilled in the art that the podiatry boot of the present invention provides many advantages over the prior art devices and the prior art use of garbage bags as protective devices. For example, the boot of the present invention is sized to fit easily over a foot with a cast or dressing without wasting material. In addition, the boot of the present invention, when properly positioned on the patient's foot has traction means on the sole, which may take the form of at least one heat seal or a strip of traction material; the traction means reduces the possibility of the user falling or otherwise having an accident. Finally, the integral fastening means of the boot makes it easy for the patient to achieve the desired watertight protective seal.

It will be readily apparent to those skilled in the art that a number of changes and modifications can be made without departing from the spirit and scope of the present invention. For example, the adhesives 19 and 22 can be the same or different and the fastening means could be a fastening web having one end bonded directly to the wall of the sock-like member. Therefore, it is intended that the invention not be limited by the description but only by the claims which follow.

We claim:

1. An improved, disposable podiatry boot made of two lay-flat sock-shaped pieces of water-impervious material heat-sealed together at their edges to form the outline of a boot with an open top, a sole portion and a leg portion, wherein the improvement comprises the addition of a permanently-affixed fastening means to one of the sock-shaped pieces near its top, said fastening means comprising:

a. an anchoring web in the form of an elongated strip of adhesive tape, having an inner and outer face, with said inner face attached along its entire length to said sock-shaped piece near its top by adhesive, and said outer face having at its proximal end an adhesive coating and at its distal end a release coating;

b. a fastening web in the form of an elongated strip of adhesive tape, having an inner and an outer face, as well as a proximal end, an intermediate portion, and a distal end; with said proximal end of said inner face of said fastening web permanently attached to said proximal end of said anchoring web by means of said adhesive coating thereon;

c. a pressure-sensitive adhesive coating on said intermediate portion of said fastening web, whereby said adhesive coating overlies said release coating on said distal end of said outer face of said anchoring web;

d. an uncoated, non-adhesive portion at said distal end of said inner face of said fastening web, wherein said non-adhesive portion of said fastening web extends past said distal end of said anchoring web, forming a tab allowing the wearer to separate said distal and intermediate portions of said fastening web from said anchoring web;

whereby said fastening means enables the wearer to wrap said leg portion of said boot tightly around his or her leg, forming a flap of loose material, and to secure said flap by pressing said adhesive-coated intermediate portion of said fastening web onto said flap.

2. The boot of claim 1, in which a further improvement comprises the addition of a plurality of heat seals in said sole portion of said boot, whereby the traction of said boot is improved.

* * * * *